United States Patent
Greenberg et al.

(10) Patent No.: US 8,501,547 B2
(45) Date of Patent: Aug. 6, 2013

(54) IMPLANTABLE MICROELECTRONIC DEVICE AND METHOD OF MANUFACTURE

(75) Inventors: Robert J. Greenberg, Los Angeles, CA (US); Neil Hamilton Talbot, Montrose, CA (US); Jordan Matthew Neysmith, Pasadena, CA (US); Jerry Ok, Canyon Country, CA (US); Honggang Jiang, Valencia, CA (US)

(73) Assignee: Second Sight Medical Products, Inc., Sylmar, CA (US)

( * ) Notice: Subject to any disclaimer, the term of this patent is extended or adjusted under 35 U.S.C. 154(b) by 0 days.

(21) Appl. No.: 13/567,366

(22) Filed: Aug. 6, 2012

(65) Prior Publication Data

US 2012/0309134 A1 Dec. 6, 2012

Related U.S. Application Data

(62) Division of application No. 12/726,274, filed on Mar. 17, 2010, now Pat. No. 8,258,635, which is a division of application No. 11/924,486, filed on Oct. 25, 2007, now Pat. No. 7,709,961, which is a division of application No. 11/592,487, filed on Nov. 2, 2006, now abandoned.

(60) Provisional application No. 60/732,884, filed on Nov. 2, 2005.

(51) Int. Cl.
*H01L 21/56* (2006.01)

(52) U.S. Cl.
USPC ............. 438/127; 257/E21.502; 257/E21.506

(58) Field of Classification Search
USPC .................... 438/64, 125–127; 257/734–786, 257/E21.502, E21.506
See application file for complete search history.

(56) References Cited

U.S. PATENT DOCUMENTS

| | | | |
|---|---|---|---|
| 4,215,156 A * | 7/1980 | Dalal et al. ..................... | 438/582 |
| 4,573,481 A | 3/1986 | Bullara | |
| 4,628,933 A | 12/1986 | Michelson | |
| 4,837,049 A | 6/1989 | Byers et al. | |
| 5,109,844 A | 5/1992 | de Juan, Jr. et al. | |
| 5,215,088 A | 6/1993 | Normann et al. | |
| 5,935,155 A | 8/1999 | Humayun et al. | |
| 6,400,989 B1 | 6/2002 | Eckmiller | |
| 6,458,157 B1 | 10/2002 | Suaning | |
| 6,516,808 B2 * | 2/2003 | Schulman ..................... | 128/899 |
| 6,900,079 B2 * | 5/2005 | Kinsman et al. ............... | 438/127 |
| 2001/0039374 A1 | 11/2001 | Schulman | |
| 2002/0120296 A1 | 8/2002 | Mech et al. | |
| 2004/0110395 A1 * | 6/2004 | Ueda et al. ..................... | 438/795 |
| 2005/0153483 A1 | 7/2005 | Groenhuis et al. | |
| 2005/0233172 A1 | 10/2005 | Schulman et al. | |

* cited by examiner

FOREIGN PATENT DOCUMENTS

WO  WO 2007/056183 A1  5/2007

*Primary Examiner* — Zandra Smith
*Assistant Examiner* — Paul Patton
(74) *Attorney, Agent, or Firm* — Scott B. Dunbar

(57) ABSTRACT

An implantable hermetically sealed microelectronic device and method of manufacture are disclosed. The microelectronic device of the present invention is hermetically encased in a insulator, such as alumina formed by ion bean assisted deposition ("IBAD"), with a stack of biocompatible conductive layers extending from a contact pad on the device to an aperture in the hermetic layer. In a preferred embodiment, one or more patterned titanium layers are formed over the device contact pad, and one or more platinum layers are formed over the titanium layers, such that the top surface of the upper platinum layer defines an external, biocompatible electrical contact for the device. Preferably, the bottom conductive layer is larger than the contact pad on the device, and a layer in the stack defines a shoulder.

19 Claims, 4 Drawing Sheets

IMPLANTABLE MICROELECTRONIC DEVICE AND METHOD OF MANUFACTURE

CROSS-REFERENCE TO RELATED APPLICATIONS

This application is a division of U.S. patent application Ser. No. 12/726,274, filed Mar. 17, 2010 now U.S. Pat. No. 8,258,635, for Implantable Micro Electronic Device and Method of Manufacture, which is a divisional application of Ser. No. 11/924,486, filed Oct. 25, 2007 now U.S. Pat. No. 7,709,961, which is a division of U.S. patent application Ser. No. 11/592,487, for Implantable Microelectronic Device and Method of Manufacture, filed Nov. 2, 2006 now abandoned, which application claims priority of provisional Application No. 60/732,884, for Implantable Microelectronic Device and Method of Manufacture, filed Nov. 2, 2005, the disclosures of which are incorporated herein by reference.

FEDERALLY SPONSORED RESEARCH

This invention was made with governmental support under grant No. R24EY12893-01, awarded by the National Institutes of Health. The federal government has certain rights in this invention.

FIELD OF THE INVENTION

The present invention is related to implantable medical devices, and is particularly related to implantable microelectronic devices.

BACKGROUND OF THE INVENTION

Biocompatibility is a critical concern for medical devices that are designed to be implanted in vivo. Biocompatibility is necessary to avoid adverse reactions in the subject, and to avoid device failure as a result of exposure to the corrosive saline body fluids and other substances in the tissue surrounding the implant. Where an implanted device includes one or more components that are not, themselves, biocompatible, it is known to provide hermetic sealing of such devices with a chemically inert coating to achieve biocompatibility, i.e., in order to avoid adverse reactions and device degradation. Many such implantable devices are intended to remain in place over long periods of time, imposing a long life requirement on the manner of hermetic sealing.

Miniature implantable medical devices commonly include microelectronic components, such as integrated circuit chips fabricated on silicon substrates. Ion beam assisted deposition ("IBAD") of alumina, often referred to an aluminum oxide ($Al_2O_3$), has been proposed for hermetically sealing such devices. Alumina has good biocompatibility, and IBAD is a useful technique for depositing dense, adherent, defect-free conformal thin films. The use of IBAD to deposit alumina on implantable medical devices is described in U.S. Pat. No. 6,844,023, entitled "Alumina Insulation For Coating Implantable Components And Other Microminiature Devices," the disclosure of which is incorporated by reference.

Most implantable microelectronic devices require means for connecting to the devices for purposes of supplying power to the device or for routing electrical signals to or from the device. Such devices include, for example, stimulators which operate by providing current to the surrounding tissue, and sensors which measure chemical or electrical properties of the surrounding tissue. When an insulator, such as alumina, is used as a coating on a device to provide hermetic sealing, a conductive path through the alumina to an external contact is typically required. For implantable devices fabricated on silicon using standard silicon processing technology, the contact pads on the device are normally copper or aluminum, neither of which is biocompatible. Thus, semiconductor device contact pads cannot simply be left exposed by patterning the surrounding alumina layer.

A prior art structure addressing the need to provide means for connecting to a sealed, implantable electronic device is disclosed in U.S. Pat. No. 6,516,808, entitled "Hermetic Feedthrough For An Implantable Device," the disclosure of which is also incorporated by reference. The '808 patent depicts several embodiments of "hermetic" electrical feedthrough structures. Thus, the embodiment of FIGS. 5A and 5B of the patent show simple via structures, while the embodiments of FIGS. 6A, 6B and 7 show "serpentine" feedthrough structure which are said to provide greater "hermeticity." Implicit in the '808 patent's discussion of the serpentine feedthrough structures, and as confirmed by the inventors hereof, is the fact that the prior art simple via feedthrough structures are not adequately hermetic, particularly in applications where they will remain in vivo for a lengthy period. While use of a serpentine structure may overcome this inadequacy, such structures are generally more difficult to fabricate and, in some instances, consume valuable "real estate" on the surface of the device.

Another approach to providing a hermetic electrical path through a conformal electrically insulating film is described in co-assigned U.S. Pat. No. 6,858,220, the disclosure of which is incorporated by reference. The '220 patent describes extremely thin (e.g., 40 nm) ultra-nanocrystalline diamond coatings wherein an electric path through the film is created by selective ion implantation. Unfortunately, this solution has limited applicability to extremely thin films that can be rendered suitably conductive by ion implantation.

Accordingly, a structure which provides better hermetic sealing of a feedthrough between an implantable microelectronic device and the surface of an encapsulating insulator is needed.

SUMMARY OF THE INVENTION

In a first aspect, the present invention is directed to an implantable microelectronic device having an electrical contact pad that is made of a non-biocompatible material; a plurality of thin, biocompatible, patterned conductive layers formed over the electrical contact pad, the top surface of the patterned conductive layers defining an electrical contact, and the first conductive layer being in direct contact with the electrical contact pad; a biocompatible electrically insulating material hermetically surrounding the device, the electrically insulating material having an aperture wherein the electrical contact is positioned. Preferably the electrically insulating material is a biocompatible ceramic, such as alumina, and the patterned conductive layers comprise one or more platinum layers formed on one or more titanium layers. The microelectronic device may be an integrated circuit chip, such that the electrical contact pad is aluminum or copper. Preferably, the first patterned conductive layer is larger in its lateral dimensions than the contact pad, such that the layer extends beyond the edge of the contact pad, forming a shoulder.

In another aspect the present invention is directed to an implantable device, comprising a microelectronic device having a conductive contact pad surrounded by electrically insulating material, at least one patterned titanium layer formed on the contact pad and extending beyond the edge of the contact pad, at least one patterned platinum layer formed over the titanium layer, the platinum layer having an exposed upper contact surface, and an alumina layer hermetically surrounding the microelectronic device and the patterned layers, the alumina layer having an aperture which exposes the upper contact surface. Preferably, the device has a plurality of patterned titanium layers and a plurality of patterned platinum layers, and one of the patterned titanium layer defines a shoulder.

In another aspect the present invention is directed to a method of making an implantable device having an electrical contact, comprising: (1) providing an electrical device having a contact pad, (2) forming a plurality of biocompatible, patterned conductive layers over the contact pad, the plurality of conductive layers having a first layer formed on the contact pad and a top electrical contact surface, (3) forming a hermetic, biocompatible electrically insulating layer over the resulting structure, and (4) forming an aperture in the electrically insulating layer to expose the electrical contact surface. Preferably, the hermetic, biocompatible electrically insulating layer is a ceramic material, such as alumina, formed by ion beam assisted deposition. Likewise, preferably the patterned conductive layers are formed by ion beam assisted deposition of metals, such as titanium and platinum, and at least one patterned conductive layer is larger than the contact pad such that it extends beyond the edge of the contact pad. In addition, preferably, at least one of the patterned conductive layers has a shoulder. The step of forming an aperture preferably comprises use of laser machining. A sacrificial layer may optionally be formed over the top electrical contact surface, such that the top electrical contact surface is protected during subsequent processing. Thereafter, the sacrificial layer may be removed.

BRIEF DESCRIPTION OF THE DRAWINGS

The foregoing aspects and the attendant advantages of this invention will become more readily apparent by reference to the following detailed description when taken in conjunction with the accompanying drawings, wherein.

Reference symbols are used in the Figures to indicate certain components, aspects or features shown therein, with reference symbols common to more than one Figure indicating like components, aspects or features shown therein.

It is noted that none of the figures used to describe the present invention are drawn to scale, and various features and dimensions are greatly exaggerated to facilitate the discussion.

DETAILED DESCRIPTION

In general, the present invention is directed to an implantable micro-miniature electronic device, and method of manufacture, with an external electrical contact surface, that has excellent hermetic properties.

Figure 1:
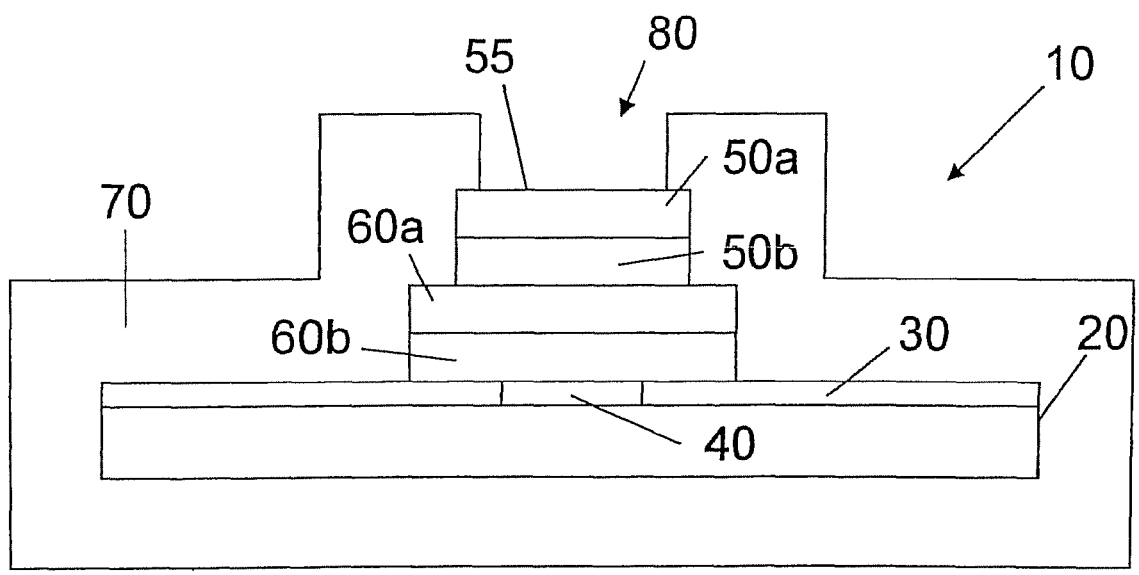
FIG. 1 is a cross-sectional view of an embodiment of the present invention.

An exemplary embodiment of an implantable microelectronic device 10 of the present invention is depicted in the simplified, cross-sectional view of FIG. 1. A silicon integrated circuit chip ("IC") 20 comprises a top electrically insulating (passivation) layer 30 and an electrical contact pad 40 which extends through layer 30 to the surface of IC 20. While the exemplary embodiment of the invention is described in conjunction with IC 20, the invention is also useful with other types of microelectronic devices, whether or not they are fabricated on silicon, which require a hermetic electrical connection. Therefore, the present invention should not be viewed as restricted to use with IC chips.

While only one contact pad 40 is shown in FIG. 1, those skilled in the art will appreciate that an IC typically has a large number of such pads. Contact pad 40 is made of copper, aluminum or aluminum alloy in accordance with standard silicon IC designs and fabrication techniques. As noted, such materials are not biocompatible and so it is necessary to hermetically isolate them. Thus, in accordance with the present invention, overlying IC contact pad 40 are multiple layers of metals, or other conductive materials, with suitable hermetic and biocompatible properties. In the exemplary embodiment depicted in FIG. 1, there are two patterned layers of, preferably, platinum 50a, 50b, formed on top of two patterned layers of, preferably, titanium 60a, 60b. Alternatively, the patterned layers may be made of iridium, palladium, niobium, titanium nitride or other biocompatible metals or metal alloys. While two layers of titanium and two layers of platinum are shown, any suitable number of layers of these, or other similar hermetic conductors may be used, as described in greater detail below. The upper surface 55 of the uppermost conductive layer, i.e., platinum layer 50a, serves as an electrical contact pad for device 10. The entire device is encased in a biocompatible electrically insulating material 70, such as alumina, which hermetically and electrically isolates IC chip 20. An aperture 80 is formed through the surrounding alumina 70 to provide access to upper contact surface 55, thereby enabling electrical connection with the device.

A feature of the present invention is that layer 60b is larger than contact pad 40 in its lateral dimensions. Thus, for example, if contact pad 40 is circular with a radius r, then layers 60b may be dimensioned to have a radius R, where R>r. Alternatively, if contact pad 40 is a square with a side dimension A, then layer 60b may have a side dimension A, where A>a. It is not necessary that layer 60b have the same shape as contact pad 40. Thus, pad 40 may be square, while layer 60b is circular. What is important, according to a feature of the present invention, is that layer 60b extends beyond the edge of pad 40 in every direction. As described in greater detail below, this provides better hermetic isolation of pad 40 and compensates for any small mask misalignments during fabrication.

Figure 2A:
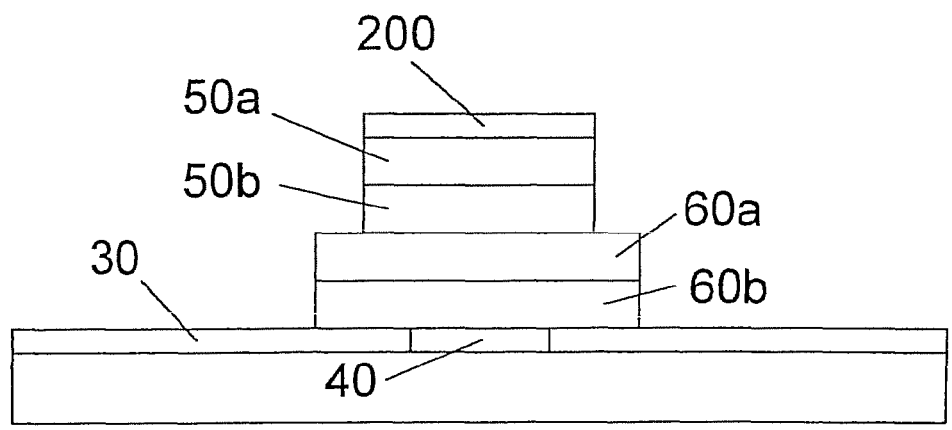
FIG. 2A is a cross-sectional view of the embodiment of FIG. 1 at an interim step during fabrication.

A process for fabricating exemplary device 10 is now described in connection with FIGS. 2A and 2B. The fabrication and design of IC chip 20, or other device used with the present invention, is not considered part of the invention and, therefore, will not be described. Multiple layers 60a, 60b, of titanium are formed on top of IC contact pad 40. As described above, while two layers are shown, any suitable number of layers may be used. In some applications a single layer of titanium may be sufficient. It will be appreciated that each additional layer adds expense and processing time. On the other hand, use of more than one layer improves hermetic properties.

According to the present invention at least the first titanium layer, and preferably all of the titanium layers, overlying pad 40 are larger in areal extent than pad 40, such that they extend beyond the entire edge of pad 40. As described above, this compensates for any inaccuracy in alignment and ensures that the surface of pad 40 is completely covered. Since a portion of the bottom titanium layer 60b is deposited on IC insulation layer 30, the insulation layer can be pretreated to promote adhesion with the titanium. Methods of pretreating may include sputtering, RIE, oxygen etch, plasma treatment or combination of two or more of these methods.

Preferably, one or more mask layers (not shown) formed by standard photolithography are used to define location of titanium deposition. Preferably, titanium deposition is done using ion beam assisted deposition ("IBAD"). Specifically, the masked IC substrate is held above a source of condensing titanium ions, while being simultaneously bombarded with ions from a plasma, such as argon. Those skilled in the art will appreciate that by carefully controlling the ion beam energy, the current density and the flux of titanium atoms, a dense, relatively defect free titanium layer can be obtained. The substrate may be rotated during the IBAD deposition of titanium to improve the uniformity of the layer. Additional layers of titanium may be deposited in like manner. In one method of implementing the present invention, rotation of the substrate is reversed with each successive layer.

If titanium is adequate for the application of implantable device 10, metal deposition could be stopped at this point. However, in accordance with a preferred embodiment, one or more platinum layers are deposited over the titanium layers. The platinum layers may be deposited using IBAD, as described above. However, the optimal process parameters, i.e., ion beam energy, the current density and the flux of atoms will differ. It is preferred, as shown in FIG. 2A, to set the diameter of the platinum layers 50a, 50b to be smaller than the underlying titanium layers 60a, 60b, so that there is an exposed shoulder or annulus of titanium 65. Titanium shoulder 65 serves as an adhesion promoter for the overlying electrically insulating hermetic material. However, use of a titanium shoulder is not necessary, and all of the conductive layers may, instead, have substantially the same diameter.

A thin sacrificial titanium layer 200 is then preferably deposited on top of uppermost platinum layer 50a to protect electrical contact surface 55 during subsequent processing. The sacrificial titanium layer may be formed in a manner similar to that described for the other metal layers, i.e., using photolithography and IBAD. It is noted that since sacrificial layer 200 is intended to be temporary, it need not have the same integrity as the other layers.

Figure 2B:
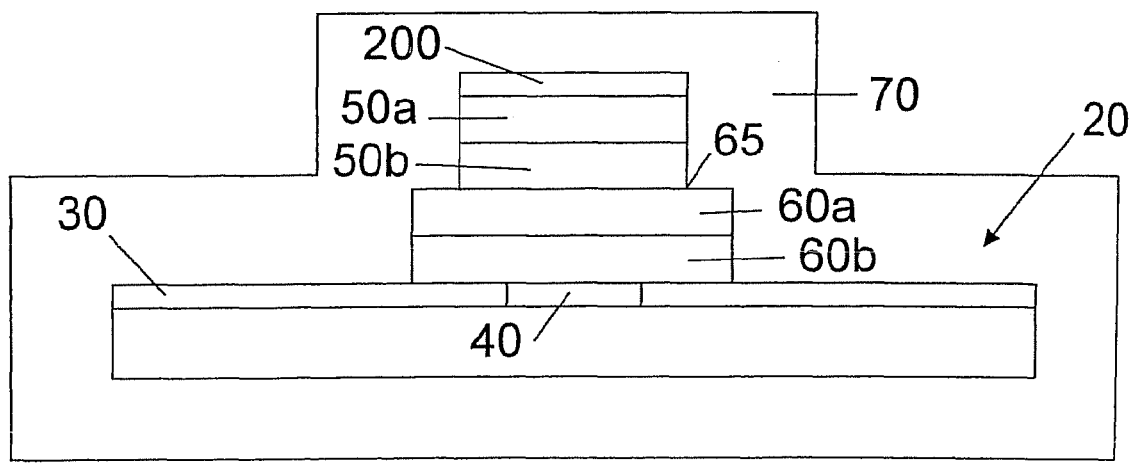
FIG. 2B is a cross-sectional view of the embodiment of FIG. 1 at a later step of fabrication.

As shown in FIG. 2B, after the various titanium and platinum layers are deposited, the entire device is hermetically encased in an insulator such as alumina. As previously noted, the surrounding alumina 70 may be deposited using IBAD in a known manner. As is known, deposition of an alumina to hermetically encase the device may require iterative processing steps whereby the device is repositioned between deposition steps such that all surfaces of the device are exposed. While this might be considered to constitute multiple layers, for purposes of the present application, these multiple layers are collectively considered to be a single hermetic layer. While use of alumina is preferred, other electrically insulating materials may also be used.

In order to obtain a long-lasting hermetic seal the material selected for encasing the device should adhere strongly to the exposed surfaces. Loss of adhesion at the interfaces between the layers due to mechanical or thermal stresses encountered during processing or thereafter can create a leakage pathway that allows fluid to migrate into the device. It is noted that shoulder 65 serves as a barrier against fluid migration in case there is a loss of adhesion between alumina 70 and platinum layers 50a, 50b. In addition, the fact that titanium layer 60b extends beyond the edge of IC contact pad 40 further provides a further barrier against fluid migration to the surface of the pad.

Titanium is preferred for use in the present invention because of its strongly adhesive properties. In particular, titanium adheres strongly both to aluminum or copper pads on an IC, and also to platinum and alumina. Titanium is not only less costly than platinum, but it also has better adherence, particularly in respect to aluminum IC pads. However, in some applications, it may be acceptable to use only platinum.

As depicted in FIG. 2B, hermetic insulator 70 completely encases the device. Thereafter, an aperture is formed through the insulator 70 to uncover the electrode structure. In one method of making the implantable device of the present invention, the aperture is created by laser drilling. Any remaining portion of sacrificial layer 200 may then be removed, such as by a suitable etching process, preferably one that selectively etches titanium. The resulting structure is shown in the previously described FIG. 1. If necessary, suitable biocompatible wires (not shown) can then be attached to surface 55, for example, by wirebonding.

Figure 3:
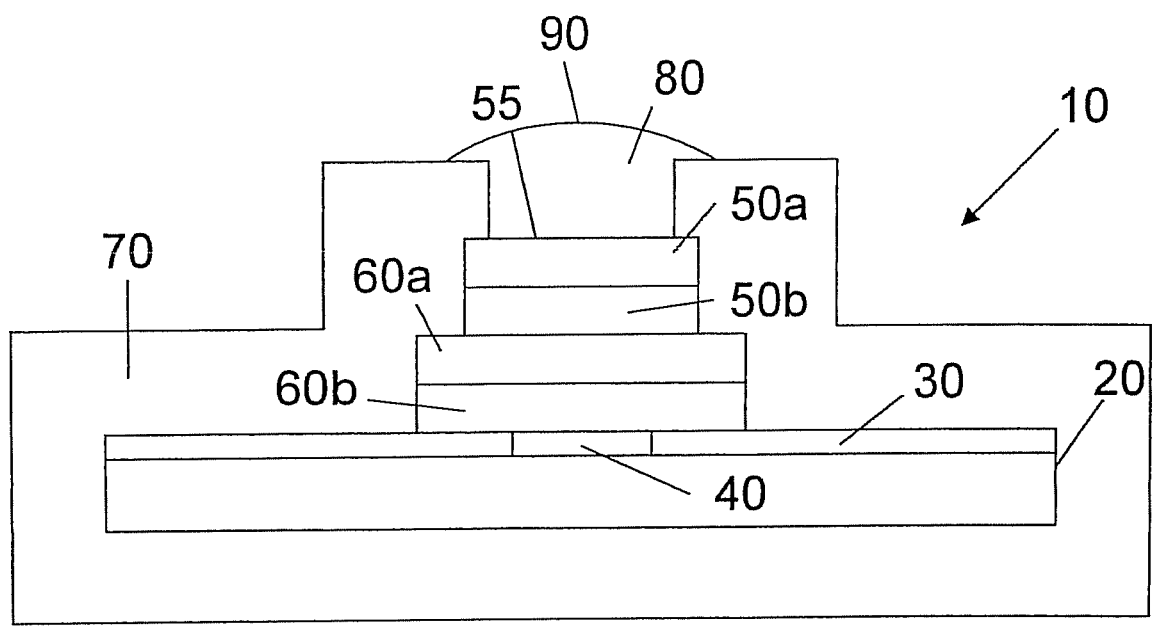
FIG. 3 is a cross-sectional view of an alternate embodiment of the present invention having a built up electrode.

Further, as shown in FIGS. 3 additional metal 90, preferably platinum, palladium, iridium or alloys thereof may be built up in the aperture 80, to improve contact with neural tissue. This may be accomplished by several processes, but preferably by electroplating. While FIG. 3 shows a mushroom shaped electrode it should be noted that the electrode may be flush or concave.

A surface of exposed, non-passivated, aluminum electrode is connected to a current driver. The current passes through this electrode into a human body. The exposed surface may be a via, or recording electrode, rather than a stimulating electrode. The exposed surface may be sircular. A metal or a combination of metals, alloys or layers, can be deposited on top of this surface. It is preferred to first deposit titanium metal in a radius that is larger than the circular aluminum metal so that it overlaps the native passivation. This ensures that the aluminum is completely covered. The titanium deposition is done by IBAD. The substrate is held above the source of condensing titanium atoms while being simultaneously bombarded by ions, typically $Ar^+$. The ion beam energy, the current density, and atom arrival rates are controlled precisely to ensure that the metal film is growing in as dense manner as possible. The holder for the substrate is rotating in order to increase deposition uniformity. A second layer of titanium may be deposited, possibly with holder rotating in the opposite direction. Two or more layers advance the hermetic film.

A final platinum layer is preferably applied. The titanium interlayer serves two purposes. The titanium allows building up some thickness of metal that will assist in hermeticity while consuming less of the more precious platinum. The titanium layer promotes the adhesion as the platinum layer adheres well to titanium but not as well to aluminum. If platinum adheres well to the base metal the adhesion layer, like titanium is not required.

The platinum metal is deposited in a similar manner although the optimal process parameters, like beam energy, current density, and atom arrival rate will differ. It is preferred to deposit two or more platinum layers in order to further ensure hermeticity. It is preferred but not essential to make the diameter of the platinum electrodes smaller than the diameter of the titanium electrodes, such that the titanium has an exposed annulus of material that will serve as an adhesion promoter to any film that may subsequently be deposited. Any number of layers of hermetic metal may be applied according to this method.

A cap layer of sacrificial metal is preferred. A sacrificial metal can be applied first if any subsequent processing of the substrate includes a process that could damage the surface of the electrode. This layer could absorb the damage and be subsequently removed, for example by etching, to expose a pristine surface of the desired metal. Titanium can be evaporated onto platinum surface to a thickness of about ≦5 µm. The subsequent exposure to a laser results in melting of the titanium. The residual titanium can be removed by an etchant, which removes the titanium but does not affect the underlying platinum.

Patterning of films deposited under harsh enviromnental conditions is achieved by ion beam assisted deposition (IBAD), which exposes the substrate to high temperature, high vacuum and ion beam bombardment. See F.A. Smidt, International Materials Reviews, 35 (1990) 61 and J. K. Hirvonen, Mater. Sci. Rep. 6 (1991) 1.

If a liftoff technique is desired only a few common photoresists survive that environment. Further a mechanical shadow mask may not be able to meet the layout design rules. The present disclosure provides a novel approach was using a polymer, like polyimide as the patterning mask. Other polymers are thermoplastic polyimide (Imidex®), epoxy resin, parylene, silicone, liquid crystalline polymer, or PEEK (Victrex®). The method is useful during the integration of stimulation electrodes onto an ASIC component. The method "Peel Off Lift Off" (P.O.L.O.) patterning, unexpected and surprisingly created high resolution, high aspect ratio, multilayer metal post structures on a silicon ASIC device.

Two methods of patterning are commonly applied in microelectronic processes, etchback and liftoff. In the etchback method a blanket layer of material is deposited on the entire substrate surface. Those areas in which the deposited material is not desired are then cleared by subtractive micromachining. The subtractive micromachining step might require photolithography or other masking prior to removal of the excess material by chemical or mechanical means. In the liftoff method a patterned mask is placed on the substrate surface prior to deposition of the additional material. The mask layer is then stripped, leaving behind the new layer only in those regions where its presence is desired.

Integrated neurostimulators can take forms of Si ASIC chips integrated with Al electrode arrays. To make the electrode array suitable for neural stimulation, the Al electrode has to be covered by other biocompatible electrode materials, such as Ti and Pt. Other conductive biocompatible metals are palladium, gold, or silver. Other conductive biocompatible materials iridium, iridium oxide or titanium nitride. The advantages of this method are: Pt and Ti coverage of Al renders the chip biocompatibility; the hermeticity provided by the metal stackup layer prevents moisture ingress to the inside of the chip during neural stimulation; and the outside Pt layer endures well of prolonged stimulation without significant corrosion and degradation.

IBAD deposition of metal Ti and Pt results to be effective in achieving those advantages. However, IBAD requires such as high temperature and low pressure. The P.O.L.O. technique provides surprising results by applying smoother conditions.

The P.O.L.O. process begins on a silicon substrate having a surface of a native oxide or passivation of additive oxide or nitride. Openings in the surface passivation exist to aluminum bond pads. Onto this substrate in wafer form is spun a 5 µm to 15 µm, preferably approximately 8 µm thick film of polyimide precursor, which is subsequently cured into polyimide. A thin film aluminum mask layer is then sputtered onto the polyimide surface and patterned using traditional dark field photolithography. The features now present as openings in the aluminum are transferred into the polyimide film using a reactive ion etch system. The aluminum bond pads on the underlying silicon substrate act as an excellent etch stop to the subsequent RIE process. The surrounding passivation material exhibits a high etch rate selectivity, which results in only a minimal removal of the material which is exposed to reactant species. The partial etch of the passivation layer may be beneficial if not overdone since the cleanliness and slight roughness created therein are conductive to stronger bonding between the metal deposit and the passivation layer.

The exposed wafer surface should be cleaned to remove any RIE residues before additional processing is performed. An ultrasonic cleaning of the wafer in DI water is applied for 3 min. After the desired openings are created in the polyimide film, the wafer is placed into an IBAD chamber for deposition of a 2 µm to 8 µm, preferably about 4 µm layer of titanium. The original thin film aluminum mask can be left in place or removed prior to IBAD processing to avoid any possible contamination of the deposited metal. When the IBAD titanium process is completed the wafer is removed from the chamber and prepared for lift off. The wafer is coated in some cases with a second IBAD film of either 1 µm to 5 µm, preferably about 3 µm platinum or titanium. The polyimide film is peeled from the silicon surface taking with it all metal from outside the desired feature locations by cleaving a sliver of wafer from the back side, and pulling it across the wafer face. The resulting wafer surface is smooth and free of residues.

The is repeated on some prototype wafers to permit the patterning of a second metal layer, of smaller diameter, on top of the first set of titanium posts. The second film contains either 3 µm platinum and/or titanium. Parts are fabricated on bare silicon wafers and passivated with nitride. Post features are laid out in an area array manner to explore the basic peel off concept, test IBAD material post adhesion, and determine the feasibility of multilayer processing (without the additional effort of polyimide planarization). A variety of post grids are tested to determine minimum pitch limits and process uniformity. This way the chosen combinations are specified. IBAD metal layers up to 7 µm thick have been successfully processed and feature sizes down to 20 µm to 30 µm, preferably about 25 µm diameter on a 100 µm to 150 µm, preferably about 125 µm pitch are achieved with >99% yield on a 3" sample.

Initial evaluation focused on the yield achieved after peeling off the polyimide mask film. For all features of 25 µm diameter or greater on a pitch of 125 µm or greater yield in excess of 99% was found after visual observation. Feature spacing proved to be a limiting factor independent of feature diameter, as the polyimide mask layer would tear in cases were adjacent feature edges were within 50 µm.

The adhesion is qualitatively evaluated using a simplified tape peel test. No failures are found between the base titanium post and the substrate. Between the stacked IBAD metal layers, failure depends on the material set. For the titanium on titanium samples, 100% of the posts remain in place after the tape is peeled. For the platinum on titanium samples, 90% of the posts remain in place after the tape is peeled.

The results are corroborated by a crude scratch shear test performed on each post stack. In this test a scalpel blade is manually dragged over the post stacks in an attempt to induce mechanical failure. For the titanium on titanium samples the blade cuts through the post while for the platinum on titanium samples the blade causes the platinum disk to separate from the underlying titanium.

These results prove that the integrity of interfaces between individual layers is critical and dependent on materials. In cases of Ti/Ti stackups, oxidation of the first Ti layer does not seem to jeopardize the integrity of Ti/Ti stickups. The oxidation is due to exposure to air after IBAD deposition and RIE of the PI mask layer for the second Ti layer deposition. However, in cases of Ti/Pt stackups, the bonding between the first Ti layer and the second Pt layer is somewhat weakened due to the oxidation of the first Ti layer, which compromises the application as neural stimulation electrodes. It has been proven that Pt sticks fairly well to Ti when it is not oxidized.

Stimulating electrode sites and basic embedded circuitry are simulated by test structure foundry wafers containing bond pads. The same technique is implemented successfully on these foundry processed wafers without negatively impacting the performance of embedded transistor elements.

This work is achieved using a crude Mylar™ mask and reflects a lower limit of the resolution capabilities. With more accurate glass photomasks successful processing of features with a minimum dimension of 10 µm up to a 75 µm pitch is achieved.

If a multilayer stack of IBAD material is desired, several configurations can be realized. A single polyimide layer can be used to pattern several sequential films so long as their total thickness is less than the mask layer thickness. Should this simple columnar structure be insufficient, the post diameter can be either reduced or enlarged for subsequent films. Alternatively, subsequent films can be deposited in other wafer locations should that be desired.

The material properties of polyimide make it suitable for use in deposition environments over a wide range of conditions. Temperatures slightly over 400° C. can be handled for durations of at least an hour and exposure to vacuum in the low millitorr range is possible.

Etched features in the polyimide layer exhibit vertical or slightly undercut cross sectional profiles due to the mechanism involved in this patterning technique. The deposited material would otherwise be deformed or even popped off the substrate surface during the mask peeling step. Proper RIE (or laser) parameters ensure the necessary wall characteristics. Release layers such as parylene, or fluoropolymer can also be applied.

FIGS. 1-4 show the sequence of the peel-off, lift-off metal patterning method. The polymer is patterned to open regions in the location and shape of the desired material features. The desired material is then deposited. After deposition, the mask polymer is peeled away from the substrate, leaving behind the deposited material in the patterned regions alone.

Figure 4:
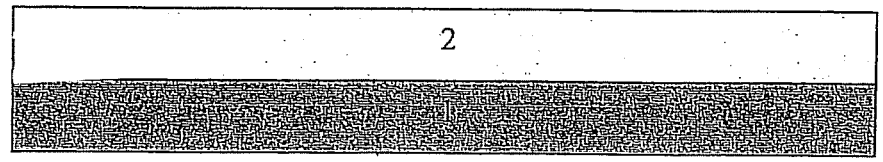
FIG. 4 is a cross-sectional view of an alternate embodiment of the present invention showing the mask deposition.

FIG. 4 is a cross-sectional view of an alternate embodiment of the present invention showing the mask deposition. This is the first step of the process, the polymer mask deposition. A polymer mask 2 is deposited on a host substrate 1. Examples of polymer deposition methods are spin coating, meniscus coating or lamination.

Figure 5:
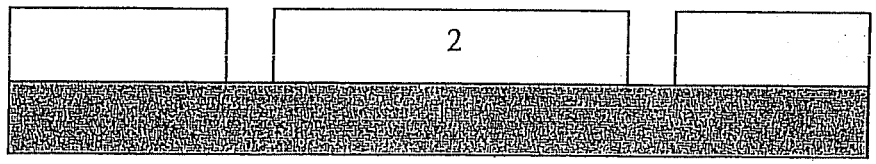
FIG. 5 is a cross-sectional view of an alternate embodiment of the present invention showing the mask patterning.

FIG. 5 is a cross-sectional view of an alternate embodiment of the present invention showing the mask patterning. This is the second step of the process, the polymer mask patterning, yielding a patterned mask polymer 2. Examples of polymer patterning methods are wet etching (liquid chemicals etc.), or dry etching (plasma, laser, gaseous chemical etc.).

Figure 6:
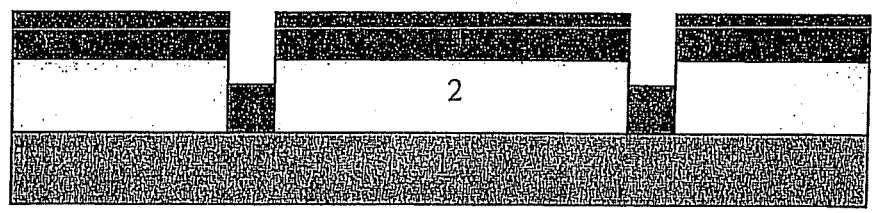
FIG. 6 is a cross-sectional view of an alternate embodiment of the present invention showing the material deposition.

FIG. 6 is a cross-sectional view of an alternate embodiment of the present invention showing the material deposition. This is the third step of the process, the material deposition yielding a deposited material 3. Examples of material deposition methods are PVD (physical vapor deposition such as evaporation, sputtering etc.), or CVD (chemical vapor deposition).

Figure 7:
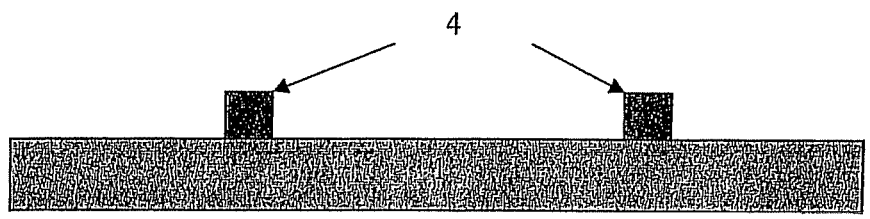
FIG. 7 is a cross-sectional view of an alternate embodiment of the present invention showing the mask polymer removal.

FIG. 7 is a cross-sectional view of an alternate embodiment of the present invention showing the mask polymer removal. This is the fourth step of the process, the polymer mask removal. This is a key difference from current Lift-Off methods which rely on decomposition (dissolution, etching etc) of the mask layer to remove it from the substrate, yielding a patterned material 4. The method described herein is also different from shadow masking, since it provides superior resolution, density, alignment and other characteristics.

The advantages of the present method are high temperature compatibility, high vacuum compatibility, chemically resistance, resistance to high energy particle bombardment, high resolution, high density, and high alignment accuracy.

The process of the present invention is particularly well suited for patterning of films deposited under harsh environmental conditions such as high temperature, low vacuum and ion or other species bombardment. One example provided in this invention is the packaging of an array of integrated electrodes for neural stimulation on an ASIC device. Stackups of biocompatible metals were successfully applied by this P.O.L.O. technique to hermetically cover the original Al that came with the integrated Si ASIC chip, making it biocompatible and therefore human body implantable.

The embodiments described above are illustrative of the present invention and are not intended to limit the scope of the invention to the particular embodiments described. Accordingly, while one or more embodiments of the invention have been illustrated and described, it will be appreciated that various changes can be made therein without departing from the spirit or essential characteristics thereof Accordingly, the disclosures and descriptions herein are not intended to be limiting of the scope of the invention, which is set forth in the following claims.

What is claimed is:

1. A method of making an implantable electronic device comprising:
   providing an electronic component having contact pads on a surface;
   applying a polymer layer to the surface of the electronic component;
   patterning the polymer layer including forming voids over the contact pads;
   applying a conductive layer to the surface including the polymer layer and the voids over the contact pads; and
   removing the polymer layer by physically pulling and peeling the polymer layer off of the surface, leaving a patterned conductive layer covering at least the contact pads.

2. The method according to claim 1, wherein the step of patterning is patterning by photolithography.

3. The method according to claim 1, wherein the electronic component is an integrated circuit having on its surface a passivation layer including openings for the contact pads.

4. The method according to claim 1, wherein the contact pads are aluminum.

5. The method according to claim 1, wherein the step of applying a polymer layer is applying polyimide.

6. The method according to claim 5, wherein the polyimide is applied between 5 µm and 15 µm thick.

7. The method according to claim 1, wherein the step of patterning includes
   sputtering an aluminum mask on the polymer layer,
   patterning the aluminum mask through photolithography, and
   patterning the polymer layer through reactive ion etch through the aluminum mask.

8. The method according to claim 7, wherein the step of patterning the polymer layer through reactive ion etch also roughens a surface of the electronic component to improve metal adhesions.

9. The method according to claim 1, wherein the step of applying a conductive layer comprises applying a titanium layer.

10. The method according to claim 9, wherein the titanium layer is applied by ion beam assisted deposition.

11. The method according to claim 10, wherein the titanium layer is applied between 2 μm and 8 μm thick.

12. The method according to claim 9, further comprising applying a platinum layer over the titanium layer.

13. The method according to claim 1, wherein the conductive layer extends beyond the edges of the contract pad.

14. The method according to claim 1, wherein the conductive layer is biocompatible.

15. The method according to claim 14, wherein the contact pad is not biocompatible.

16. The method according to claim 1, further comprising applying an insulating layer over the electronic component defining voids over the conductive layer, but smaller than the conductive layer.

17. The method according to 16, wherein the insulating layer is ceramic.

18. The method according to claim 17, wherein the ceramic is alumina.

19. The method according to claim 16, wherein the insulating layer and the conductive layer form a hermetic seal around the electronic component.

* * * * *